United States Patent [19]

Tarr, Jr. et al.

[11] Patent Number: 4,960,417
[45] Date of Patent: Oct. 2, 1990

[54] COMPACT TAMPON APPLICATOR WITH IMPROVED INTERLOCK

[75] Inventors: Warren T. Tarr, Jr., Turners Falls; Irl R. Sanders, III, Wilbraham, both of Mass.

[73] Assignee: Tambrands, Inc., Lake Success, N.Y.

[21] Appl. No.: 220,164

[22] Filed: Jul. 18, 1988

Related U.S. Application Data

[63] Continuation-in-part of Ser. No. 60,832, Jun. 12, 1987, Pat. No. 4,846,802, and Ser. No. 68,994, Jun. 19, 1987, abandoned, which is a continuation of Ser. No. 879,140, Jun. 26, 1986, Pat. No. 4,726,805.

[51] Int. Cl.$^5$ .............................................. A61F 15/00
[52] U.S. Cl. .................................................... 604/15
[58] Field of Search ........................ 604/11, 13, 14, 15, 604/16, 18, 904

[56] References Cited

U.S. PATENT DOCUMENTS

| | | |
|---|---|---|
| 3,015,332 | 1/1962 | Brecht ..................................... 604/15 |
| 3,148,680 | 9/1964 | Roberts et al. . |
| 3,699,962 | 10/1972 | Hanke . |
| 3,765,416 | 10/1973 | Werner et al. . |
| 3,895,634 | 7/1975 | Berger et al. . |
| 4,271,835 | 6/1981 | Conn et al. . |
| 4,361,150 | 11/1982 | Voss et al. . |
| 4,479,791 | 10/1984 | Sprague . |

FOREIGN PATENT DOCUMENTS 3812987 2/1989 Fed. Rep. of Germany ........ 604/11

Primary Examiner—John D. Yasko
Assistant Examiner—Anthony M. Gutowski
Attorney, Agent, or Firm—A. Thomas S. Safford

[57] ABSTRACT

A shortened tampon applicator of the telescoping tube type employs an ejector tube to store a tampon at its distal end and an outer tube disposed by a slip fit thereover. Directionally-locking inward flaps fixed within the distal end of said outer tube engage the distal end of the tampon stored in the ejector tube thus securing the latter relative to said outer tube while permitting only distal expulsion therefrom. The ejector tube advantageously has inwardly biased short stubby fingers at its distal end which catch behind the proximal end of the tampon. Preferably, the applicator tubes are both molded form soft plastic and have an improved restraining means for interlocking the two tubes. This means comprises a stopping ring and a shorter adjacent inner stabilizing ring positioned to project from the inner surface of the outer tube at its proximal end and an axially overlapping a third ring of ribs positioned around the outer surface of the ejector tube near its distal end. The positioning and shape of the stabilizing third ring relative to the other two rings serve to decrease wobble and to increase the tube interlock strength, among other advantages.

22 Claims, 8 Drawing Sheets

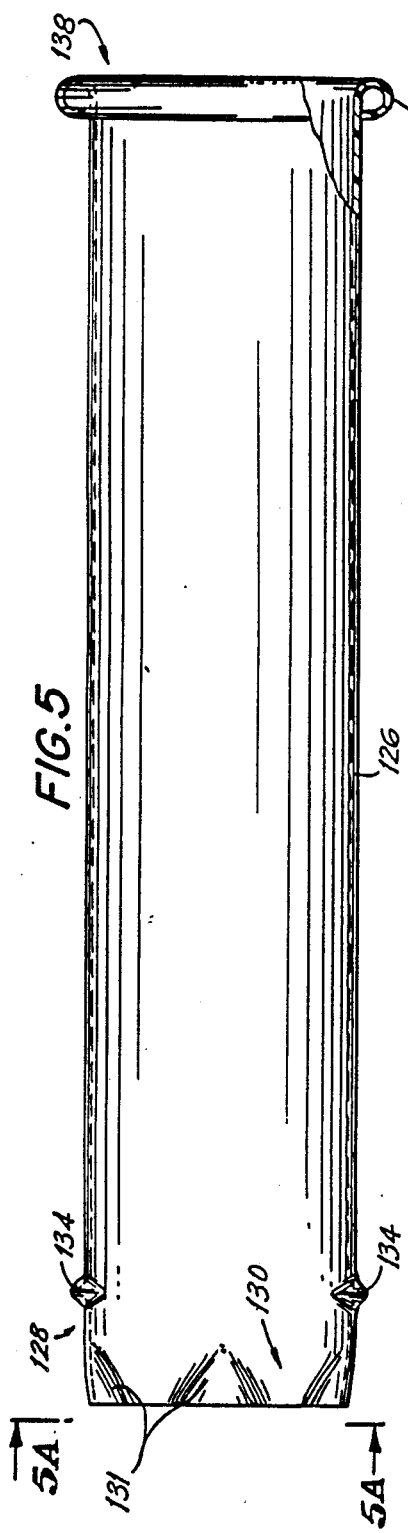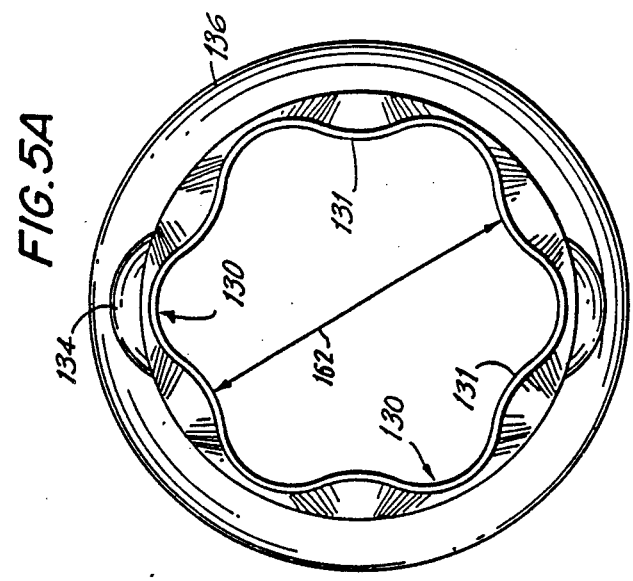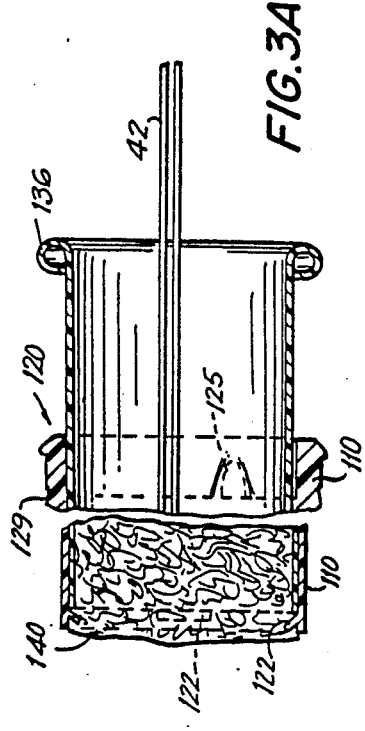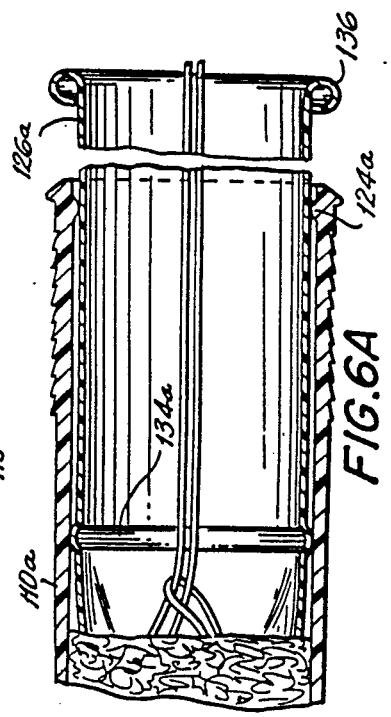

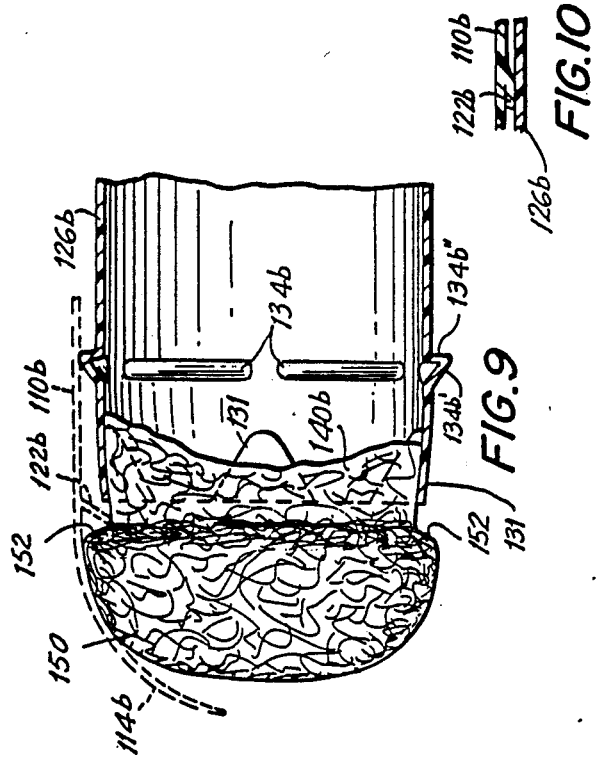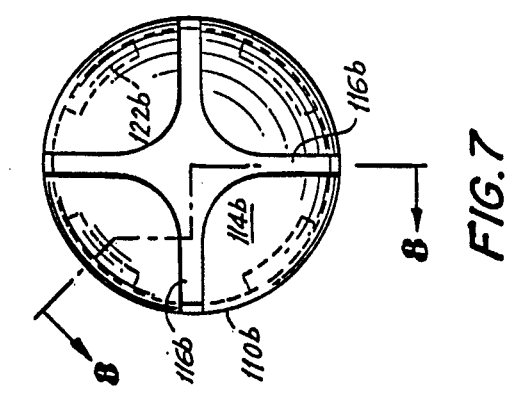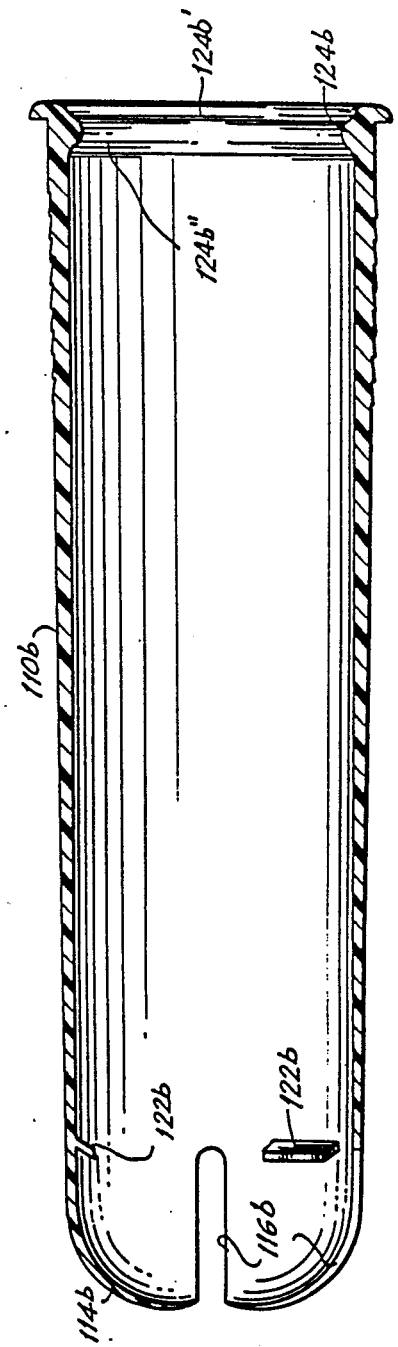

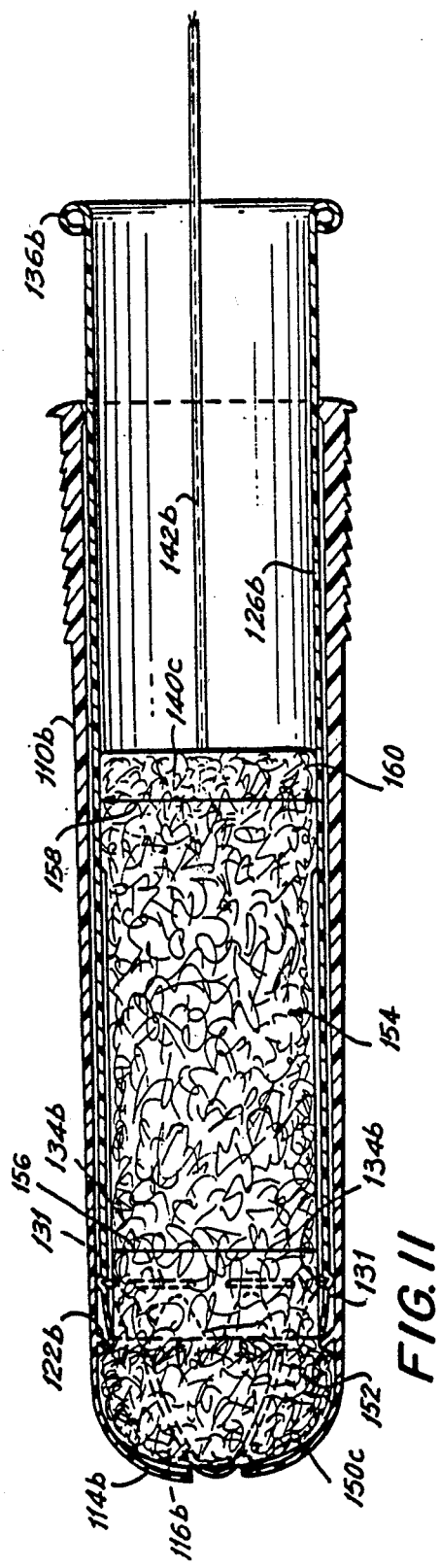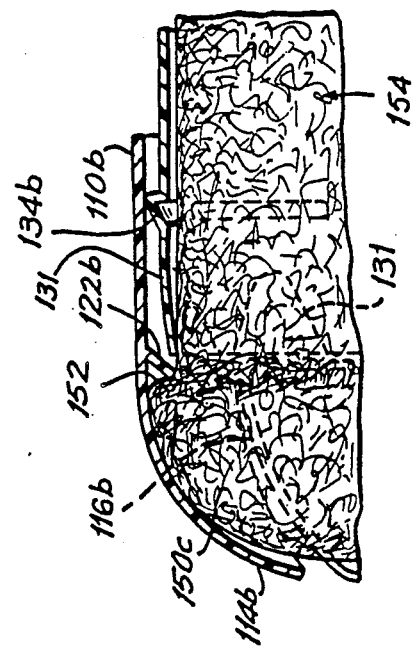

FIG. 13
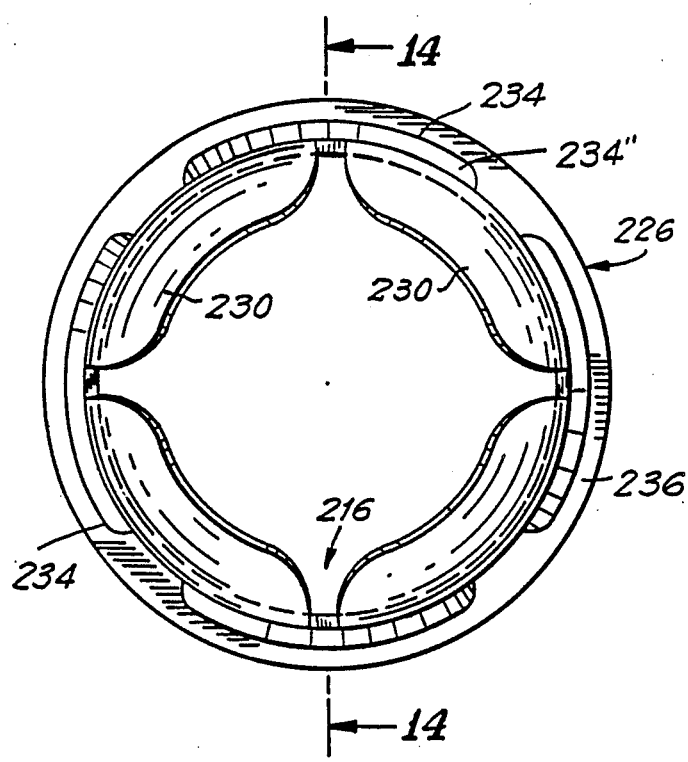
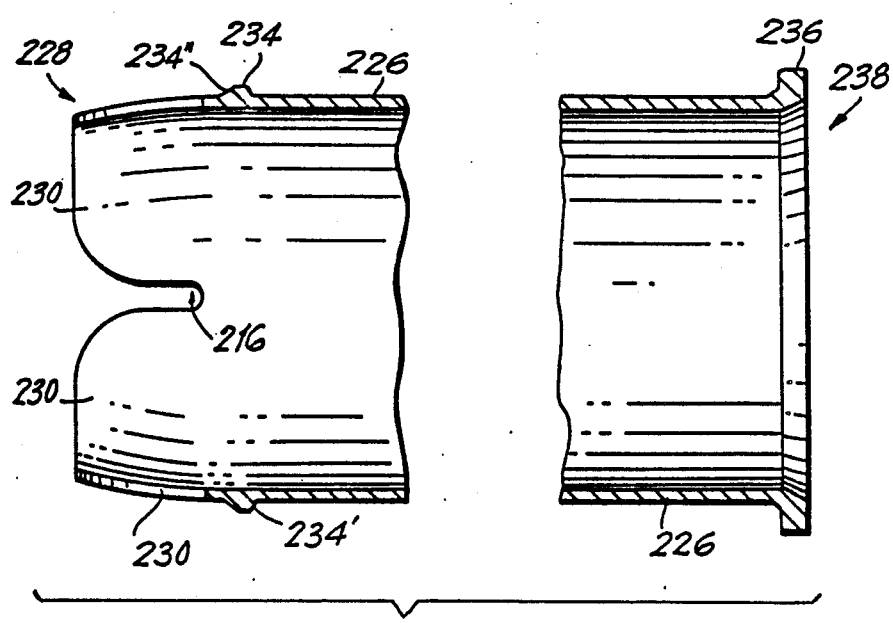
FIG. 14

COMPACT TAMPON APPLICATOR WITH IMPROVED INTERLOCK

This is a continuation-in-part application of copending application Ser. No. 060,832 filed June 12, 1987, now U.S. Pat. No. 4,846,802 (and of the identical duplicate application initially separately identified as Ser. No. 068,994 filed June 19, 1987, now abandoned), which is a continuation of application Ser. No. 879,140 filed June 26, 1986 copending therewith (and now issued as U.S. Pat. No. 4,726,805 on Feb. 23, 1988).

This invention relates to tampon applicators and, more particularly, is directed to compact catamenial tampon applicators of the type employing telescoping tubes, and specifically is inclusive of new restraining means for interlocking said tubes.

BACKGROUND OF THE INVENTION

Most commercially available tampon applicators for introducing catamenial tampons intravaginally consist of a pair of telescoping tubes. See, for example, U.S. Pat. 3,696,812. The outer tube is designed to store a tampon at one end. The inner or ejector tube is slightly smaller in diameter and is slidably positioned behind the tampon carried in the outer tube. In use, the tampon is ejected from the applicator by pushing the inner tube into the outer tube to expel the tampon.

Several drawbacks are associated with such applicators for certain uses. For example, such tampon applicators are substantially longer than the tampons. First, the outer tube must be of length sufficient to assure proper depth of insertion. Next, when the tampon and outer tube are assembled with the ejector tube, a major portion of the latter tube necessarily extends out from the end of the outer tube. This results in the over-all length of the packaged ready-for-use tampon applicator being approximately two and one-half times the length of the tampon. As a result of such a relatively large size, the bulk and cost of the packaging for such applicators are increased.

Women commonly carry such packaged tampons (with applicators) in their purses. Because of the length of such applicators, they occupy a relatively large amount of space in the purse. It is therefore also desirable to produce a tampon applicator of smaller size which is less obtrusive. This is a particular problem for younger women who often prefer not to carry purses and with today's fashions often must use pockets in relatively tight-fitting clothes.

Another type of tampon applicator has been proposed to solve the foregoing problems by telescoping the ejector tube completely into the outer tube while storing the tampon in the distal end of the ejector tube. This also shortens the tampon and applicator assembly by the length of a tampon. Operatively, the ejector tube (often referred to as the pusher tube) is "cocked" by being withdrawn proximally out most of the way from its stored position in the outer tube (leaving behind the tampon) until the distal end of the ejector tube is positioned to engage the proximal end of the stored tampon. Each patentee discloses a different way of securing the stored tampon in the distal end of the outer tube to prevent proximal displacement of the tampon while the ejector tube is withdrawn therefrom. See U.S. Pat. Nos. 2,832,342; 3,090,385; 3,101,713; 4,276,881; 4,286,595; and 4,479,791; and British Patent No. 2,033,754.

Apparently, none of the foregoing types of applicators has ever been commercially successful.

Applicators of the conventional telescoping tube type typically include a restraining means to prevent disassembly. See, for example, ribs 20 on one cardboard tube interacting with grooves 18 on the other in U.S. Pat. No. 3,696,812, and similarly see interference ribs 32 and 38 respectively, on opposing plastic tubes in U.S. Pat. No. 3,148,680.

Interlocking restraining means became more important in preventing disassembly in the compact applicator designs, because the added cocking step needs to be controlled to prevent disassembly. These earlier designs also tend to be inadequate, particularly for the compact applicators, because of often being subject to wobble in the fully cocked position. The tendency to wobble is also more likely in molded plastic applicators, which because of manufacturing requirements, are made from tubes which are slightly tapered.

Also, in a compact applicator, the diameters of inner and outer tubes must be more nearly the same, than in the type shown in U.S. Pat. No. 3,148,680, to make room for storing the tampon within the inner tube without the outer tube being too bulky. Thus, interference ribs 32 and 38 cannot be as large in a compact applicator and are thus less effective. This could be somewhat compensated for by making the tubes from a stiff plastic, but this is not functionally nor commercially acceptable. Too stiff a plastic would be too brittle and also would result in an uncomfortable and even injurious applicator (scratching and pinching delicate tissue). Typically the stiffness, measured as the flexural modulus (ASTM D790 procedure), in a tampon applicator should not exceed 90,000 psi. Thus, a compact applicator made from acceptably soft plastic with reasonably small interference ribs normally would not have an effective restraining means for adequately interlocking the telescoping tubes to prevent disassembly in normal use.

OBJECTS AND SUMMARY OF THE INVENTION

Accordingly, it is an object of this invention to provide a tampon applicator that overcomes the above-described difficulties.

More particularly, it is an object of this invention to provide a commercially acceptable tampon applicator which is compact and of reduced size.

It is another object of this invention to provide a tampon applicator which is simple in construction and in manufacture and is convenient and easy to use.

It is a further object of this invention to provide a tampon applicator which permits the use of an ejector tube which is simple to assemble, without radial orientation problems, and can be made from soft molded plastic preferably by injection molding with an improved restraining means for interlocking telescoped tubes without wobble and preferably with audible or sensible seating in the cocked position.

It is a still further object of this invention to provide a tampon applicator which can be handled and assembled in conventional machinery without major machine redesign.

In accordance with a preferred embodiment of this invention, a tampon applicator includes an ejector tube adapted to store a tampon therein. An outer tube is slidably disposed over the ejector tube. The outer tube is adapted to pass the tampon through its distal end during an ejection operation. Directionally locking inwardly-projecting flaps are circumferentially affixed at or near the inner distal end of the outer tube for engaging the distal end of a tampon which is stored in the distal end of an ejector tube, which in turn is telescopically positioned in the outer tube. These flaps function so as to prevent movement of the tampon in the proximal direction. Preferably, the flaps abut the distal end of the ejector tube. Despite the surprisingly small and relatively fragile size and the circumferential shape and placement of these flaps, they are unexpectedly effective (even though positioned very close to the distal ends of the tampon and of the outer tube). Thus, when the ejector tube is partially withdrawn from the outer tube so as to be positioned behind the tampon, the flaps are effective to fix the tampon relative to the outer tube. However, when the ejector tube is forced distally back through the outer tube so as to eject the tampon therefrom, the flaps permit the forward displacement and expulsion of the tampon.

In cocking the ejector tube when initiating the use of the applicator, it is commercially important that the ejector tube and the outer tube not become disassembled. An improved restraining means to prevent this comprises three ring-like structures positioned between the two telescoped tubes, with one ring pair on one tube axially overlapping one ring on the other tube (or vice versa). The ring pair comprise a stopping ring and a shorter adjacent inner stabilizing ring, which both preferably are positioned to project inwardly from the inner surface of the outer tube at its proximal end. The third ring-like structure preferably is in the form of a plurality of (e.g. four) circumferentially-aligned ribs spaced about 5° to 15° apart and positioned on the outer surface of the ejector tube near its distal end. The preferred slope of each of the sides of the rings and the ribs is approximately 30° to the axis of the respective tube, although this can vary some (and the proximal slope of the ribs can be 60° or even 90°). The preferred overlap between the ribs and the stabilizing ring is about 0.0035 inches and the overlap between the ribs and the stopping ring is about 3½ times more. This is a sufficient overlap adequately to impede disassembly of telescoped tubes made from soft plastic (without hindering the initial mechanical assembly in the other direction).

The positioning and shape of the stabilizing third ring relative to the other two rings serve surprisingly to improve over the conventional two ring restraining means so as to both control wobble and increase the tube interlock strength (i.e. the force needed to effect disassembly). To be effective the ring of ribs must contact the facing slopes of both the stopping ring and the stabilizing ring, and the stabilizing ring must be shorter than the stopping ring. This permits the use of shorter rings and softer (more desirable) plastic for the tubes, while maintaining adequate interlock strength and minimal outer tube diameter relative to the tampon size. The wobble seems to be controlled initially by the ribs being shaped to interfit with the conformation of the valley formed between the ring pair. If the ejector tube is angled relative to the outer tube (as occurs when there is wobble), the ribs in the conventional two ring restraining means would merely rock against the abutting stopping ring on one side and skid inwardly away from the ring without restraint on the other side. However, with the stabilizing ring, the ribs on both sides are captured in the valley between the ring pair and when displaced by the wobble are forced to slide up the sloping sides of the valley thus radially squeezing the ribs and resisting the wobble.

In the preferred embodiment, the valley has a flat bottomed cross-section about 0.02 inches wide with sides angled at about 30°, and the ribs are compatibly shaped. In other words, the ribs have a plateau of the same width, with a matching diameter, and with at least the distal slope of the ribs matching the facing proximal slope of the stabilizing ring.

The stabilizing ring preferably also has a relatively long plateau on the order of 0.12 inches. In this embodiment, the ribs are formed on the outside of the ejector tube at a distance from its distal end of at least the length of the plateau of the stabilizing ring. Thereby such distal end, which is normally radially spaced from the outer tube (including said ring pair), is brought to bear on the stabilizing ring plateau and further resist any loose wobble. Without a stabilizing ring the loose wobble of the conventional restraining means has a 10° deflection, which in contrast the addition of a stabilizing ring in the form of the aforementioned embodiment reduced this to a 1% deflection.

It is believed that the valley formed between the stabilizing ring and the stopping ring, by tending to immobilize the ribs after the latter have been snapped in place during the "cocking" step, serves to give the increased tube interlock strength which has been observed. This increase in strength was observed in a test on "regular" size tampon applicators of comparable dimensions, differing essentially only with respect to the presence or absence of the stabilizing ring. The presence of the stabilizing ring increased the strength by roughly 50% for both soft and stiff plastic, as follows:

| Straight Pull | |
|---|---|
| Without stabilizing LDPE | 1097.5 grams |
| With stabilizing LDPE | 1511.5 grams |
| Without stabilizing PP | 810 grams |
| With stabilizing PP | 1410 grams |
| 5° Angle Pull | |
| Without stabilizing LDPE | 720 grams |
| With stabilizing LDPE | 1095 grams |
| Without stabilizing PP | 592 grams |
| With stabilizing PP | 1067 grams |

The straight pull was in line with the axis of the outer tube and the angled pull was at 5° to that axis. LDPE is low density polyethylene while PP is polyproplyene.

As can be seen from the foregoing table, disassembly of the tubes is easier (requires less strength) as the tubes became misaligned (i.e. at an angle to one another) Since the stabilizing ring tends to minimize wobble to 1% or less, it thus further decreases the likelihood of disassembly.

A further unexpected advantage of the stabilizing ring is the sensory signal which is conveyed to the user at the end of the "cocking" step. The resistance from the interference fit of the ribs sliding over the plateau of the stabilizing ring gives an initial "warning" to the user. Then, as the slightly compressed ribs slide off the plateau of the stabilizing ring, they apparently hit against the stopping ring with an audible and slightly tactile snap. This serves to alert the user instinctively that the applicator is fully cocked and ready for subsequent use in the conventional manner.

Yet another unexpected advantage of the stabilizing ring is a corollary to being able to maintain tube interlocking strength without increasing ring height when using softer plastics. This design permits much easier removal of the outer tube from the core pin during the molding procedure allowing greater cycling for a given time and reducing product spoilage due to deformed or otherwise damaged tubes.

The outer tube advantageously has petals at its distal end. The ejector tube may be formed from extruded tubing with resilient circumferential undulations at its distal end or preferably by injection molding with stubby inwardly-curved fingers at the distal end. These undulations or fingers are urged outwardly when a tampon is loaded into the ejector tube through the proximal end, i.e., during manufacture. When used by the ultimate consumer, the ejector tube is partially withdrawn from the proximal end of the outer tube to the fully "cocked" position with the applicator ready for vaginal insertion of the tampon, and the distal end of the ejector tube is thus disposed behind the tampon so that these undulations or fingers are free to close in behind the tampon and engage the proximal end of the latter.

The undulations or stubby fingers should not extend inwardly too much. Otherwise, they might grip rather than slide over the tampon during the proximal withdrawal of the ejector tube and (1) thus undesirably stretch the compressed tampon longitudinally and (2) consequently also still grip the tampon at the end of the proximal withdrawal (thus preventing the ejector tube from expelling the tampon by the subsequent distal stroke of the ejector tube).

The crimped flutes, which form the undulations heat set in the proximal end of the plastic ejector tube, can be subject to loss of shape due to plastic creep. This can result from prolonged storage of the tampon and applicator assembly, where the undulations are flattened between the stored tampon and the outer tube. With such relaxation in the plastic due to creep, the undulations may not close inwardly sufficiently behind the tampon when the ejector tube is withdrawn into the cocked position. This can result in the tampon slipping at least partially back into the ejector tube during the distal pushing stroke of the ejector tube, resulting in at least incomplete expulsion of tampon. The applicant has successfully overcome this and other problems by the surprising expedient of having the tampon diameter 0.005 to 0.030" smaller at the shoulder adjacent its distal head end relative to its proximal tail end.

Conversely, certain kinds of tampons may be made from a sufficiently springy material, such that the undulations may not be needed at all. In such a case, the thickness of the ejector tube may be sufficient to engage the proximal end of the tampon effectively to assure reliable expulsion.

Advantageously, the ejector tube may be made from molded plastic with inwardly curved fingers at its distal end. However, these preferably are short and thus relatively strong and are adapted to slide over the tampon upon withdrawal of the ejector tube and automatically to close inwardly behind the tampon sufficiently to engage the end of the latter. Plastic creep is not a problem because the fingers are originally formed in the curved shape, rather than being subsequently heat set into that final shape.

The outer tube is preferably also injection molded of plastic synthetic resin.

In this specification and the accompanying drawings, we have shown and described preferred embodiments of our invention and have suggested various alternatives and modifications thereof, but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it and embody it in a variety of forms, each as may be best suited to the conditions of a particular use.

BRIEF DESCRIPTION OF THE DRAWINGS

FIGS. 1 to 10 also appear in priority U.S. Pat. No. 4,726,805;

FIG. 1 is a partially sectioned longitudinal view of a prior art tampon applicator according to assignee's U.S. Pat. No. 4,479,791;

FIG. 2 is a longitudinally sectioned view of the tampon applicator of FIG. 1, (but with an alternative embodiment of a portion of the restraining means 34c), showing the fingers of the ejector tube expelling the tampon from the outer tube;

FIG. 3 is a longitudinally sectioned view of a preferred embodiment of a tampon applicator according to the present invention;

FIG. 3A is a detail of a view similar to FIG. of an alternative preferred embodiment showing a tampon and applicator assembly where the outer tube has no petal sections at its distal end;

FIG. 4 is a longitudinally sectioned view of the outer tube portion of the embodiment of FIG. 3;

FIG. 5 is an elevational side view (partially-sectioned) of the ejector tube of the embodiment of FIG. 3;

FIG. 5A is an end view of the distal end of the ejector tube of FIG. 5;

FIG. 6 is a longitudinally sectioned view of the embodiment of FIG. 3 showing the ejector tube pushing a tampon out the distal end of the outer tube;

FIG. 6A is a detail of an embodiment similar to FIG. 6 but modified such that the tube restraining means are changed to a fully circumferentially-extending detent ring axially overlapping a similar single stopping ring, which are respectively formed on the outer distal end of the ejector tube and the inner proximal end of the outer tube;

FIG. 7 is a distal end elevational view of a still further modified preferred embodiment of an outer tube similar to that shown in FIG. 6A;

FIG. 8 is a longitudinally sectioned view taken on angled line 8—8 of the outer tube shown in FIG. 7;

FIG. 9 is a longitudinally sectioned view of the distal end of the ejector tube for the applicator embodiment shown in FIGS. 7 and 8 containing a modified compression-hardened tampon having an enlarged head, a portion of the outer tube from FIG. 8 is shown in dotted outline;

FIG. 10 is an enlarged sectional detail of certain structures of FIG. 9, but relatively shifted to the expelling position (showing a flap flattened to permit the ejector tube to pass thereby);

FIGS. 1 to 12 also appear in priority U.S. Pat. No. 4,846,802;

FIG. 11 is a longitudinally sectioned view of the applicator embodiment shown in FIGS. 7 to 10 containing a further modified tampon having a smaller diameter body with an enlarged head and a slightly enlarged tail;

FIG. 12 shows an enlarged portion of FIG. 11, better showing the small clearance between the tampon and the ejector tube at the shoulder area of the tampon;

FIGS. 13 to 16 depict as preferred embodiments newly disclosed restraining means for interlocking the tampon applicator tubes;

FIG. 13 is a distal end view of a modified preferred embodiment of the ejector tube molded from FIG. 14 is a truncated longitudinally sectioned view of the ejector tube of FIG. 13 showing ribs for the restraining means with adjacent stubby distal fingers;

FIG. 15 is an enlarged sectional detail of a preferred embodiment of an improved restraining means shown partially on the inner proximal end of an outer tube similar to that shown in FIG. 8 and partially on the outer distal end shown in dash-dot outline of the ejector tube of FIGS. 13 and 14; and FIG. 16 is similar to FIG. 15, showing the ejector tube with a modified shape to the detent rib and with the outer tube in dash-dot outline.

DESCRIPTION OF COMMON ASSIGNEE'S EARLIER DEVELOPMENT

Figure 1:
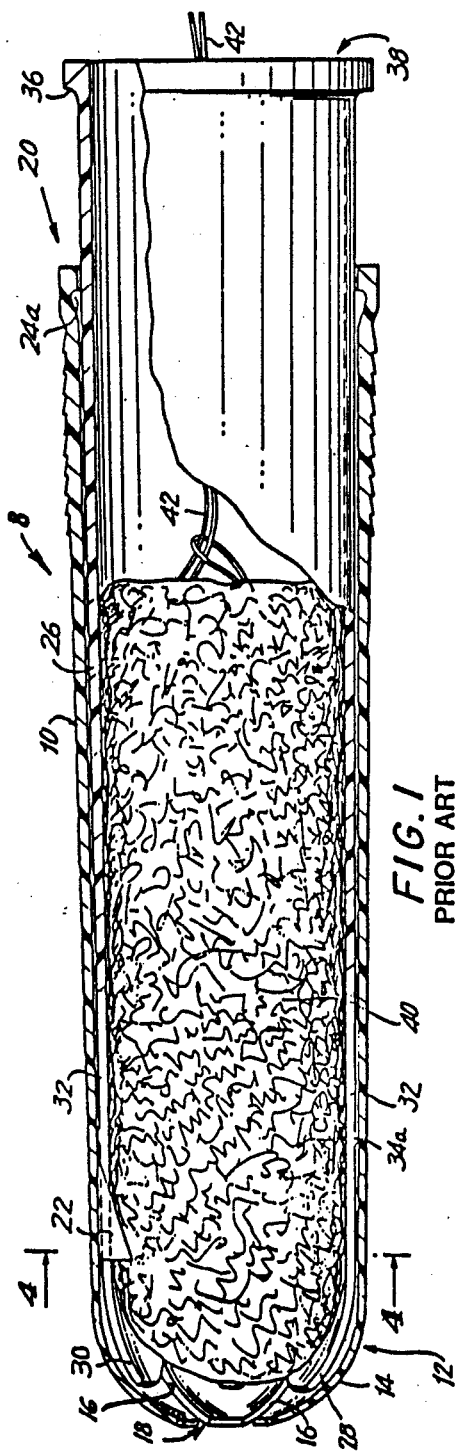
Figure 2:
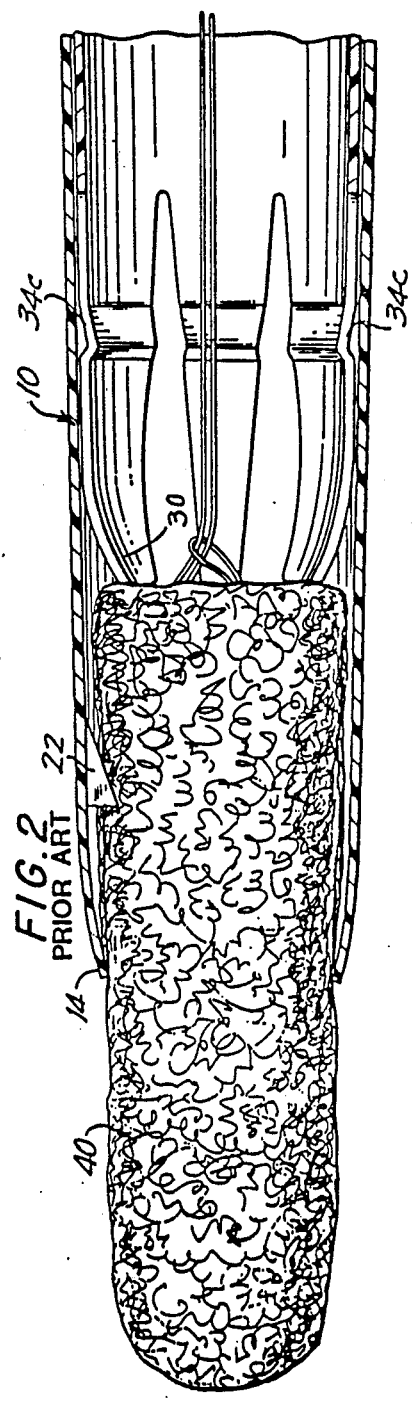

FIGS. 1 and 2 illustrate embodiments of the tampon application 8 of U.S. Pat. No. 4,479,791 (incorporated herein by reference), of which the present invention is a surprisingly simplified and effective improvement.

The cylindrical outer tube 10 has at its distal end 12 conventional petal sections 14 which are separated from each other by respective slots 16. The petal sections 14 are made relatively flexible and are normally biased in a substantially arcuate closed configuration to form a rounded tip having a central opening 18 at the distal end 12. This rounded shape of the distal end 12 helps facilitate the insertion of the applicator into the vaginal cavity. Such outer tubes 10 are preferably constructed from any suitable smooth plastic material. The opposite or proximal end 20 of the outer tube 10 is open.

The outer tube 10 further includes an unconventional plurality of inward projections 22 formed along an inner circumferential portion thereof. These projections 22 are of a substantially flat, right triangular configuration with the long side thereof extending at an acute angle from the inner wall of the outer tube 10 towards the central opening 18. The projections 22 extend inwardly from the outer tube 10 sufficiently to engage a catamenial tampon 40 disposed therein. Unless made quite wide, these axially extending projections 22 may have a tendency to roll over and become inoperative, especially, if the tampon has a relatively hard surface from a high degree of compression. The outer tube 10 as shown in FIG. 1 includes an annular groove 24a along an inner circumferential portion of the proximal end 20.

The tampon applicator 8 illustrated in FIG. 1 further comprises an inner or ejector tube 26. This serves as a hollow plunger for ejecting a tampon 40 positioned within the distal end of the outer tube 10. The ejector tube 26 is dimensioned to slidably move within the outer tube 10, with minimal clearance therebetween. The ejector tube 26 is also preferably slightly longer than the outer tube 10 to assure complete ejection and proper depth of placement of the tampon 40. Being hollow, the ejector tube also permits proper placement of the withdrawal string 42. The distal end 28 of the ejector tube 26 is formed with a plurality of fingers 30 which are separated from each other by slots or openings 32 through which the projections 22 of the outer tube 10 extend to engage the tampon 40 disposed therein. In the same manner as with petal sections 14 of the outer tube 10, the fingers 30 are made so as to be slightly biased towards a closed configuration, as shown in FIGS. 1 and 2.

In order to limit the axial movement of the inner tube 26 relative to the outer tube 10, each such finger 30 further includes a raised detent or rib 34a to coact with the groove 24a as a restraining means. The placement of these can be reversed (for example, see groove 34c in FIG. 2 which would coact with a corresponding rib 24c [not illustrated]). The ejector tube 26 also includes an outwardly directed circumferential retention flange 36 at its proximal end 38.

DETAILED DESCRIPTION OF PREFERRED EMBODIMENTS OF THE INVENTION MAINLY DISCLOSED AND PARTIALLY CLAIMED IN PRIORITY U.S. PAT. NO. 4,726,805

A preferred embodiment of the applicator assembly 108 incorporating the principles of this invention is shown in FIGS. 3 to 10.

Elements in this embodiment, which are identical with those in the illustrated prior art device shown in FIGS. 1 and 2, are identified with the same reference numbers. Analogous structural features in tis embodiment are identified with the same reference numbers, but raised by 100.

Figure 3:
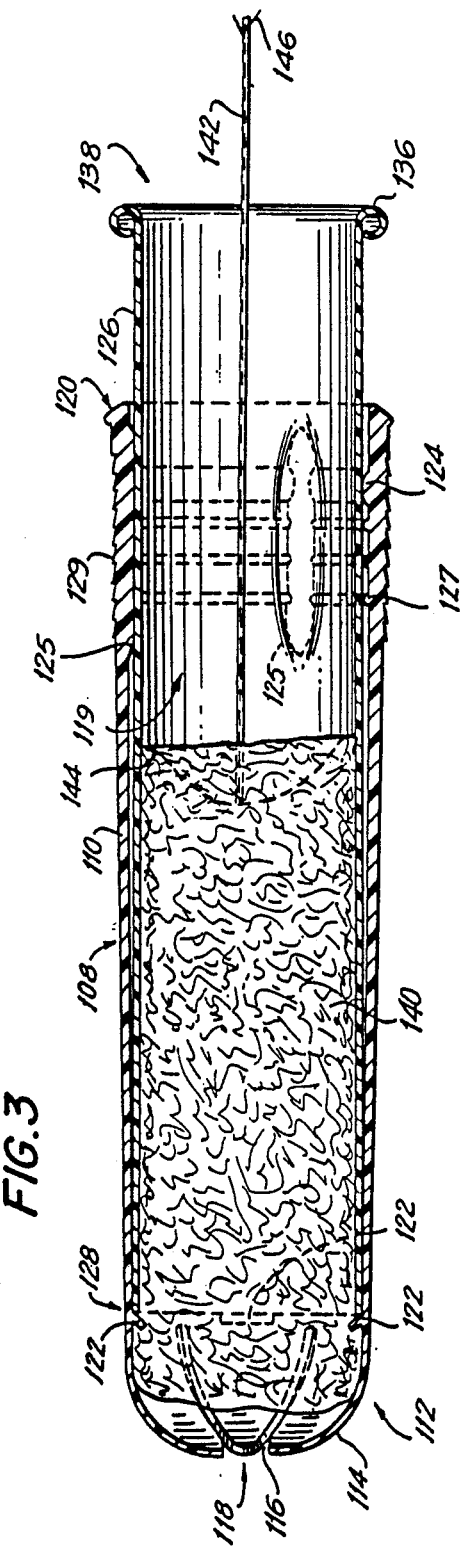

In the embodiment of FIG. 3, a cylindrical outer tube 110 (FIG. 4) has at its distal end 112 a plurality of petal sections 114 defined by slots 116, and converging to a central opening 118. The tampon 140 is stored in the distal portion of the central cavity 119 of the tube 110, and is held in place by one or more flaps 122 (shown in FIG. 4B, see also FIGS. 7 and 8). Preferably, four such flaps 122 are provided, one disposed approximately at the base of each respective petal section 114.

These flaps 122 are disposed in an inward direction generally perpendicular to the axis of the outer tube 110 and are preferably canted towards the distal discharge end thereof.

An optional outer ridged or knurled finger gripping surface 129 at the proximal end of the tube 110 provides the user with a secure finger grip of the outer tube 110.

As shown in FIGS. 3 and 5, the inner pusher or ejector tube 126 is disposed within the outer tube 110 and over the stored tampon 140. The distal end 128 of the tube 126 preferably abuts the flaps 122 in the stored position (FIG. 3). As shown in FIGS. 5 and 5A, the distal end 128 is preferably provided with a plurality of undulations 130 (e.g., six).

Figure 6:
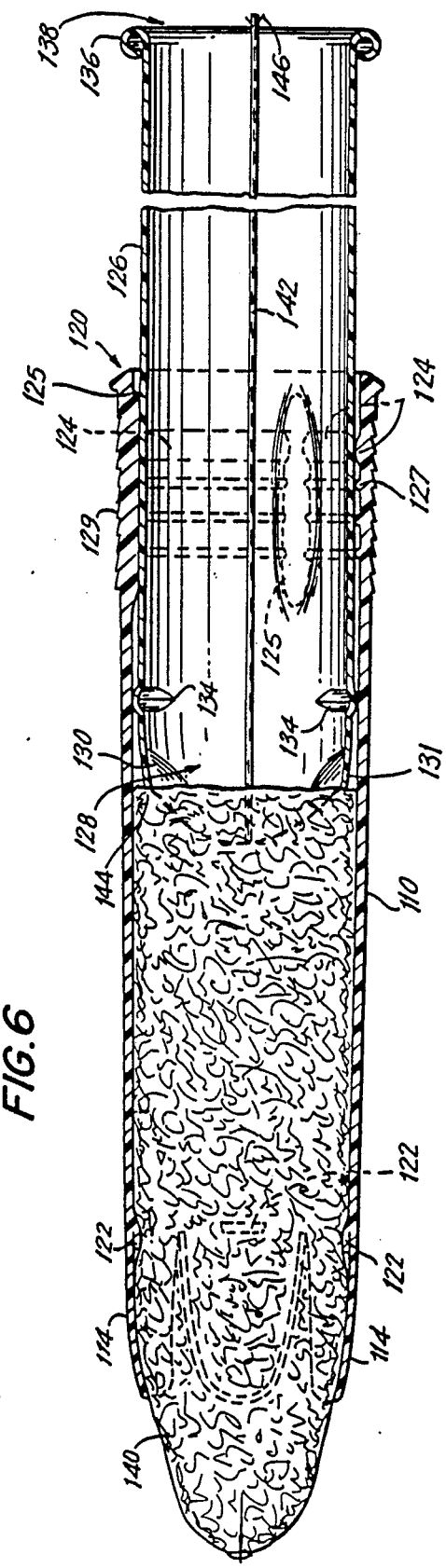

The undulations 130 are resiliently flexible, so that in the stored position, as shown in FIG. 3, the inner portions 131 of the undulations 130 are biased flexibly outward by the carried tampon 140. This permits the undulations 130, and the remainder of the tube 126, to pass over the tampon 140 that is secured in the outer tube 110 by the flaps 122, during partial withdrawal of the ejector tube 126. Then, because of the stiff flexibility of the undulations 130, when the ejector 126 is sufficiently withdrawn as shown in FIG. 6, at least the inwardly directed portions 131 of these undulations 130 will flex inwardly to a lesser diameter 162 than that of the tampon 140. Consequently, when the discharge tube 126 is moved forwardly, i.e. in the distal direction, the tampon 140 will be engaged at its proximal end by undulations 130, and thus urged out the distal discharge end 112 of the outer tube 110.

As shown in FIGS. 3 and 6, the distal or base end of the tampon 140 may be uniquely formed with a concave configuration leaving a more dense center and a relatively softer peripheral ridge 144. The softer ridge 144 aids the proximal end of the tampon 140 in catching on the undulations 130, thus serving as an unidirectional lock to prevent the tampon 140 from re-entering the ejector tube 126 during expulsion.

An even more reliable and effective alternative embodiment to enhancing the function of the undulations 130 is accomplished by use of a two-diameter (or equivalent) tampon, see FIG. 11. Because the compressed tampon is stored inside the inner ejector tube 126, it displaces (forces outwardly) the crimped flutes 131 (undulations) in the distal end of the plastic ejector tube 126 flattening the flutes 131 against the inner surface of the outer tube 110. Over a period of time under this force the plastic relaxes (creeps) such that the flutes 131 will not spring back to their original (preassembled) minimum inside diameter 162 after the inner ejector tube 126 is withdrawn from around the tampon 140.

If the resulting minimum inside diameter is too large, the tampon 140 can be at least partially forced back inside of the ejector tube 126 during the expulsion stage, which can cause functional difficulties or failure (by incomplete expulsion, improper positioning, or the like).

The two-diameter tampon 140c shown in FIGS. 11 and 12 reduces the amount of creep by reducing the diameter of the tampon 140c at least in the area of the contact points between the ends of the flutes 131 and the body of the stored tampon 140c. In the preferred embodiment, this provides a differential of the tampon shoulder inner diameter 156 (i.e. the accommodation diameter) to the tampon tail diameter 158 such that the net effect of any creep is reduced, thus ensuring reliable operation. In other words, the minimum inside diameter 162 (see FIG. 5A) of the flutes at the ends of the ejector tube 126b when in the cocked position is effectively less than the diameter 158 of the tampon tail 160. This assures positive engagement of the undulations 131 against the proximal tail end of the tampon 140c during the expulsion step. Advantageously, the accommodation diameter 156 remains constant along the major portion of the tampon body 154. This reduces strain on the flaps 122b. However, the transition from the accommodation diameter 156 to the larger tail diameter 158 can be sloped, etc. (so the two-diameter shape per se is not critical).

Preferably, the diameter 162 of the tampon 140c at its tail 160 (the proximal end) approximates the inside diameter of the ejector tube 126b.

The ejector tube 126 can be functional even without undulations 130, or the like, if the tampon 140 is sufficiently expansive to fit closely within the outer tube to ensure positive engagement by the unmodified distal end of the ejector tube against the proximal end of the tampon during the ejection step.

Alternatively, in a preferred aspect of this invention the distal end 228 of the molded plastic ejector tube 226 can have fingers 230, similar to the fingers 30 of tube 26, but considerably shorter so as to avoid orientation problems and to give a stronger structure. This alternative is commercially preferred because such stubby inwardly-curved fingers are not subject to plastic creep. The fingers 230 are short enough to remain proximally behind the flaps and thus avoid any orientation problem.

As described below, the fingers 230 also co-act with the stabilizing ring 270 to limit the play or wobble of the ejector tube when in the locked position within the outer tube.

The outer tube 110 is preferably tapered at a small angle $\theta$ (see FIG. 4) towards the distal discharge end of the tube 110. This facilitates removal of the formed tube 110 from the molding apparatus. This is true of the ejector tube as well, if it is also molded.

IMPROVED TUBE INTERLOCK

FIGS. 13 to 16 illustrate a restraining means with significantly improved features over even the interlock structures shown in U.S. priority Pat. No. 4,726,805. In the preferred embodiments illustrated in these latter figures, the stopping ring 224 is formed at the proximal inner end 220 of the outer tube 210. This ring 224, interacting with the ring of four ribs 234 on the proximal end of ejector tube 226, serves as the principal restraining means for preventing the disassembly of the ejector tube 226 from the outer tube 210. However, the effectiveness of the restraining means is greatly enhanced by the additional feature of an appropriately placed and configured stabilizing ring 270.

Ring 270 decreases wobble and misalignment, increases interlock strength, and provides a means for giving an audible and/or tactile indication to the user that the applicator is properly locked ready for use with the ejector tube 226 in the fully extended position. This gives the significant advantage of keeping the radial size of the restraining means relatively small, thus minimizing the outer diameter of the outer tube for a given tampon size, while at the same time permitting the use of relatively soft plastic (for greater customer comfort and acceptance), without the necessity for "beefing up" the wall thickness to compensate for the softness.

Tubes molded from typical polypropylene having a stiffness (measured as the flexural modulus, ASTM D790) of 150,000 to 200,000 psi can be interlocked by the older conventional two ring restraining means of the type shown in the U.S. Pat. No. 3,148,680. However, tampon applicators having stiffness of 10,000 to 90,000 psi, and especially the more preferred range of 10,000 to 40,000 (typical of the soft resins like low density polyethylene or linear low density polypropylene, which latter ranges from 15,000 to 80,000 psi) are much more difficult to lock together, except by the present invention.

The maximum diameter of the ribs 234 is generally less than the inner diameter of the outer tube 210, while the minimum diameter of the stopping ring 224 is generally more than the diameter of the ejector tube 226. Thus the telescoped tubes 210 and 226 are interfit relatively loosely, except when ribs 234 engage rings 224 and 270. The radial overlap between the ribs 234 and the stopping ring 224 is sufficient to give an effective interlock (including an interference fit with the stabilizing ring 270). Preferably, this unique restraining means would have a disassembly force in the range of 1000 gms to 1600 gms, measured as a straight pull.

The height and spacing of the stabilizing ring 270 relative to the stopping ring 224 is enough to prevent wobble where the ejector tube is extended to the cocked position with the ribs 234 seated in the valley 272 and one tube is grasped and the applicator is at least lightly shaken with a tampon 240 loaded in place. This would simulate minimal customer acceptability.

The lead-in slope 270" of the stabilizing ring 270 can vary considerably so long as the force to draw the ribs up the slope 270" is substantially less than the disassembly force needed to draw the ribs up the slope 224" of the stopping ring 224. Slope 270" would preferably range from 10° to 30°.

Figure 15:
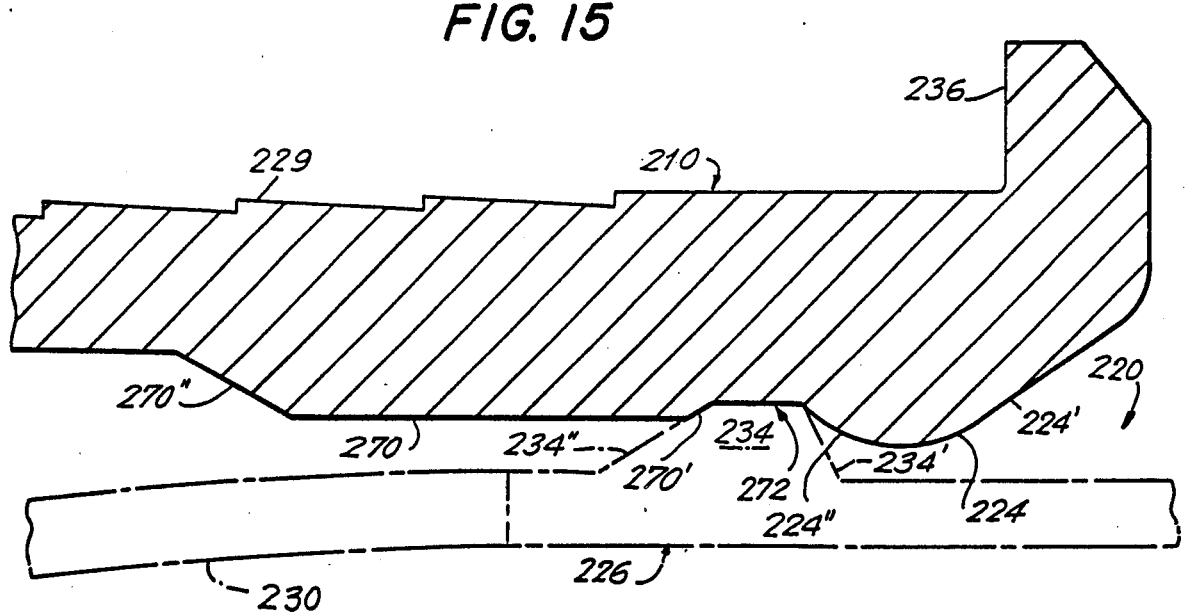
Figure 16:
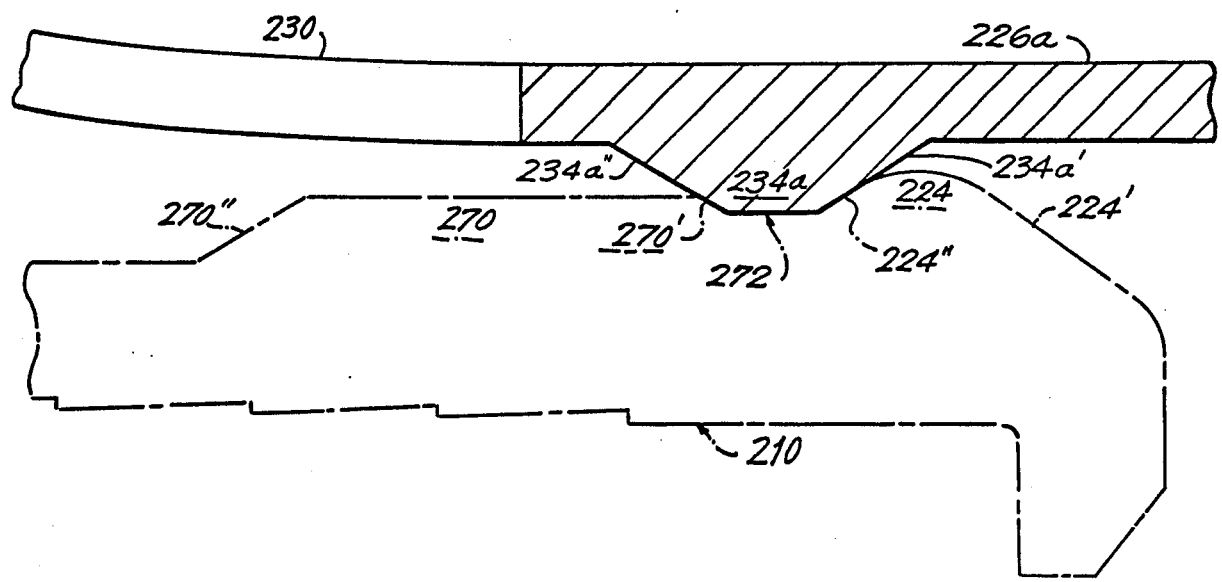

Because of the small radial dimensions available between the principal diameters of the facing surfaces of tube 210 and 226, the conformation of the upper part of the ribs 234 and of the valley 272 should be substantially the same, preferably, with the top of the rib 234 being flat and of the same width as the correspondingly flat valley 272 and with the slope 234" matching that of slope 270', although the slope 234' of the rib 234 may be more abrupt (e.g. 60° or 90°) than the slope 224" (e.g. 35°) of the stopping ring 224 (see FIG. 15). Compare FIG. 16, where the slope 234a' of the modified rib 234a, desirably, more nearly conforms to the slope 224" of the stopping ring 224. Slope 224" could advantageously range from 33° to 60°. Again, the configuration can be changed so long as the function of having the rib 234 seated in the valley 272 can resist being displaced therefrom by riding up a slope 224" or 270' as the rib 234 is displaced in either the proximal or distal direction.

The slope 224' serves as an assembly aid in the initial manufacture when the ejector tube 226 carrying a tampon extending slightly from its distal end is inserted at the proximal end 220 of the outer tube.

Cost considerations will serve to keep the width of the stabilizing ridge from being too great, but it should preferably be enough to limit the angular displacement of the ejector tube 226 relative to the outer tube 210 by engaging the fingers 230 as the tube 226 is rocked about the rib 234 when seated in the valley 272 (this would be a clockwise rotation in FIG. 15).

Similarly, the rib 234 (and the corresponding valley 272) should not be unnecessarily wide, but advantageously has some breadth sufficient to aid in minimizing the wobble between the tube 226 and 210.

The illustrated straight lines of the various slopes and plateaus could be slightly curved or modified in shape, if the main functions are maintained.

EARLIER TUBE INTERLOCKS

Figure 4:
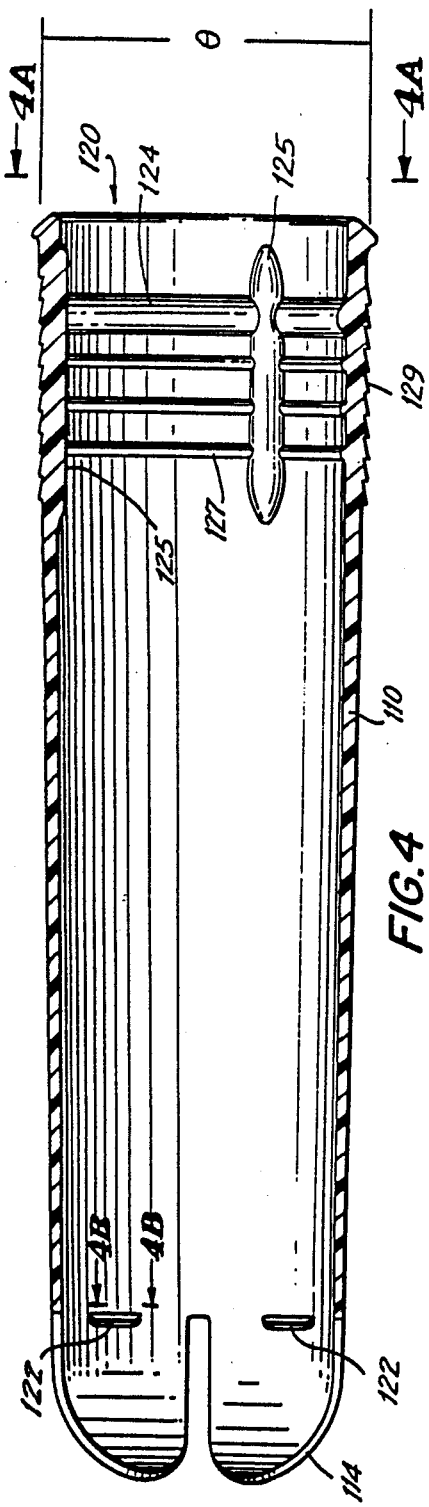
Figure 4B:
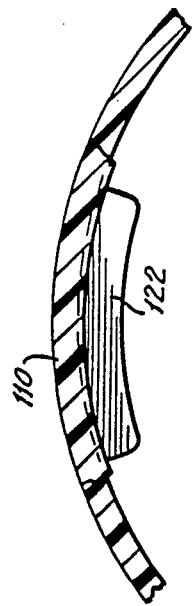
FIG. 4B is a sectional view taken at line 4B—4B of a portion of the distal end of the tube of FIG. 4.
Figure 4A:
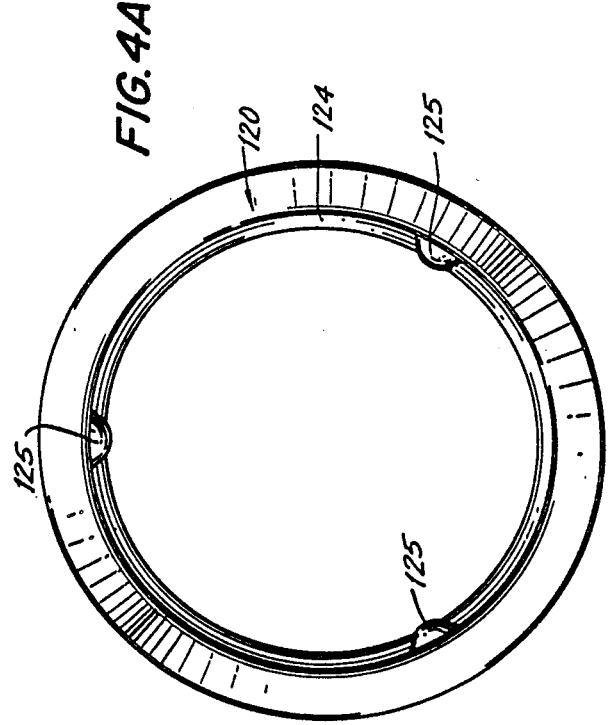
FIG. 4A is an end view of the proximal end of the tube of FIG. 4.

FIGS. 4 and 4A also show another type of restraining means previously developed by applicant's assignee. This was developed to compensate for the slightly tapered shape of the molded outer plastic tube of FIG. 4 relative to the cylindrical shape of the extruded plastic inner tube of FIG. 5.

A stopping ring 124 is provided on the inner surface of the outer tube 110 near the proximal end thereof. A plurality of detents 134, preferably two (see FIGS. 5 and A) to six (see FIG. 9), are circumferentially aligned and extend radially outwardly from the ejector tube 126 near its distal end 128. The ring 124 instead of being a continuous ring, could also be made of a plurality of circumferentially aligned segments.

These two members 124 and 134 act together as the restraining means to reduce the chance of complete withdrawal of the inner ejector tube 126 from the proximal end 120 of the outer tube 110 during the proximal movement of the ejector tube 126 prior to the discharge of the tampon 140.

Longitudinal ribs 125 and annular ribs 127 may also be provided on the interior of the proximal end of the outer tube 110. These help compensate for the taper in the outer tube and to give a better fit between tubes 110 and An alternative more preferred, unidirectional, restraining means is illustrated in FIGS. 8 and 9. In this latter preferred means, the six raised detents 134b each have in one direction an angled sloping face 134b' (for example, 60° to the axis) and a perpendicular face 134b" in the other direction (to permit easy initial assembly and yet to prevent disassembly). In the preferred stopping means, the ribs 125 and 127 are omitted, leaving only ring 124b on the inner wall of the outer tube 110b. This has an inner slope 124b" relative to the longitudinal axis of about 35° to permit withdrawal from the mold in which it was formed. Otherwise, a more perpendicular slope would be appropriate. The opposing slope 124b' approximates 45° to 50°.

For contrast, a more conventional restraining means is shown (which is less effective for the many reasons previously given). As shown in FIG. 6A, the detents 134 are replaced by a single complete circumferential raised detent ring 134a. The stopping ring 124a and the raised detent rib 134a are rounded (without the more positive locking perpendicular face 134b"); however, they similarly axially overlap to inhibit disassembly of the tubes 110a and 126a. This is somewhat similar to the structure in U.S. Pat. No. 3,148,680.

At its proximal end 120, the extruded tube 126 is rolled outwardly to form an annulus 136, serving as a retention flange.

The flaps 122 engage the forward, or distal portion of the tampon 140 and prevent its proximal movement when the ejector tube 126 is partially withdrawn. However, as shown in FIG. 6, these flaps 122, preferably, are distally inclined and as such tend to securely grip a tampon against proximal movement (much the way a speed nut functions, making a unidirectional jamming engagement). Yet these flaps 122 bend (distally) out of the way when the ejector tube 126, and the carried tampon 140, are moved distally (during assembly and during customer use), thereby aiding the unidirectional free movement of the tampon 140. Compare the flaps 122 in FIGS. 3 and 6; see also flaps 122b in FIG. 10.

The unique and unexpected effectiveness of the flaps 122 can best be appreciated by comparison to the prior art illustrated in FIGS. 1 and 2. The prior art projections 22 are shown as longitudinally-extending broadly-based pointed wedges. These are shaped and placed to extend towards the proximal end. They are not canted nor are they flexible in the axial direction. They require that the ejector tube 26 have elongated fingers 20 (so as to pass clear of the wedges during the expulsion operation and also during assembly and to avoid undesirably increasing the overall length of the stored tampon and applicator assembly). However, as most dramatically shown in FIGS. 3A and 8, applicant preferably uses circumferentially extending flaps, which eliminates the need for fingers. These circumferentially-extending flaps are unexpectedly effective not only in engaging the tampon 40 advantageously almost at its very distal end, but also, doing so with a structure having a minimal longitudinal and radial extent. This permits the use of an ejector tube 126 which can be blunt ended (i.e. no finger slots 32).

This elimination of at least long fingers 30 gives several significant advantages. An ejector tube 26 with long fingers 30 must be rotated for axial alignment of the slots 32 with the projections 22, requiring more complicated and expensive assembly machinery. Even with such machinery, the manufacturing reliability is probably decreased, increasing risk of quality control problems.

Tampons come usually in three traditional sizes; regular, super, and super plus. In a typical plastic applicator embodying the present invention, the "super" size advantageously will have dimensions as described below. The molded outer tube 110 at its distal end has an inner radius of about 0.3" and a wall thickness of about 0.02". The four flaps 122 subtend an axial angle of about 40° (and would thus be approximately 0.2" transversely), are about 0.015" thick axially, extend radially inwardly about 0.04" from the tube 110, and are canted distally at a 60° angle to the axis thereof. Thus the linear tip portion (in the free end) of the flap 122 is oriented distally relative to the base portion (i.e. the end where the flap joins the outer tube 110). The extruded plastic ejector tube 126 has a constant outside radius of about 0.28" and a wall thickness of between 0.01–0.02". Thus, the flaps 122 might, typically, extend only about 0.02" into the tampon 140 stored within the end of the ejector tube 126, and yet, these reliably secure the tampon 140 relative to the tube 110 during proximal withdrawal of the tube 126. From this, it can be seen that the flaps 122 in fact can be made to extend radially inward only little more than the thickness of the ejector tube 126. Yet, this is adequate unidirectionally to hold the tampon.

Sometimes, tampons which are highly compressed while dry form a relatively hard surface. This would typically occur occasionally only in the smaller size "regular" tampons. This would typically occur occasionally in the smaller size "regular" tampons. It may be difficult sometimes for flaps 122 to grip reliably in all cases into such a surface. In such circumstances, the tampon 140b may preferably be formed with a slight head 150 at the distal end to provide an abrupt shoulder 152. As shown in FIG. 9, this shoulder 152 provides a positive catching point for the flap 122b to bear against so as to resist proximal withdrawal of the tampon 140b. See also FIGS. 11 and 12.

As a further feature, the tampon head 150 is advantageously formed with a rounded shape to closely underlie the soft smooth petals 114b of the outer tube 110b to give adequate support to the petals to prevent the user from being pinched in the slots 116b, see FIGS. 7 to 12. The tampon head 150 can achieve this purpose without extending to the very end of the petal tips (thus leaving room for a slight longitudinal expansion of the stored tampon). If the tampon head is not needed to support the petals 114b, then it can be quite short longitudinally (just enough to give substance to the shoulder 152), see for example the dimensions shown in FIG. 3A (where no petals are used).

For an applicator of these general dimensions, the transverse dimension of the flaps 122 range from about 1/16 to ¼", and preferably, range from ⅛ to 3/16". Any more than ¼" would tend to reduce flexibility and tend to increase the resistance to expulsion of the tampon. However, within the broader aspects of this invention, the flaps 122 could be a single 360° flap, either continuous or slit at discrete intervals to form a series of closely spaced or abutting flaps.

The size, shape, placement and number of flaps can be varied, as can the flexibility, the material used for construction, and angle of distal canting; so long as the desired function of unidirectional securing of the tampon is achieved. However, in order to obtain the advantages of this invention, the flaps must be dimensionally greater in the circumferentially transverse direction than in the axial direction. They preferably should be essentially closely adjacent to the circumferentially continuous portion of the distal end 112 of the outer tube 110 and advantageously, should be essentially in circumferential alignment with one another. Without such alignment, then to keep the same overall assembled length, the ejector tube 126 would become somewhat unnecessarily shortened. Preferably, an inscribed circle tangentially touching each canted flap would have a diameter slightly smaller than the diameter of the stored tampon at the points of contact between the flaps and the tampon.

The petal sections 114, with the slots 116, make that portion of the distal end 112 of the outer tube 110 circumferentially discontinuous. If the flaps 122 are positioned right at the base of the petal sections 114, they can still function reliably, but if positioned much further out on the sections 114, then the flexibility of the sections 114 would hamper the effectiveness of the flaps 122 by permitting the flaps to swing free of the tampon 140 with which they are designed to coact. The curvilinear aspect of blade-shaped flaps 122 with the two relatively pointed corners (as best shown in FIG. 4B) serves to aid in the effectiveness of the flaps. The inner "blade" edge of the flaps could advantageously be serrated, if an increased unidirectional grip were deemed necessary for a particular tampon.

Referring to one preferred embodiment in FIG. 3, the assembled tampon-and-applicator 108 is shown ready for packaging, with the ejector tube 126 being substantially within the outer tube 110. See a similar, more preferred embodiment in FIG. 11. A tampon 140 is stored within the ejector tube 126, not directly in the outer tube. The tampon is comprised of an absorbent material formed into the general shape of an elongated cylinder and having attached to its rearward portion a withdrawal string 142, as is conventional in the art. The withdrawal string 42 in the prior art in FIGS. 1 and 2 is shown doubled to form a loop locking the two loose ends. It is shown in FIGS. 3 and 6 as a single string 142 sewn to the tampon pad by thread 146. The outer tube 110 is telescoped over the ejector tube 126 so that the distal ends 126, 128 of the two tubes 110, 126 are closely adjacent to one another. It is thus readily apparent from FIG. 3 that the dimension of the tampon applicator 108 in that illustrated preferred embodiment in its stored configuration is approximately 1.8 times the length of tampon 140 in contradistinction to previously-described conventional commercial telescoping tube applicators having a length of two and one-half times that of the tampon stored therein. The length of the improved applicator is now controlled primarily by the insertion depth desired (which determines the length of the outer tube) rather than by the applicator design requirements. Note that where a tampon has been compressed longitudinally as well as transversely, it is typical that there is provided some allowance for longitudinal elongation (due to absorption of ambient moisture while stored in the applicator).

In operation, outer tube 110 is firmly held at the finger grip area 129 while ejector tube 126 is partially withdrawn therefrom (i.e. ejector tube 126 is axially moved in the proximal direction away from central opening 118). During this activating or "cocking" step, the tampon 140 remains in a fixed position relative to outer tube 110 by means of the flaps 122 which grip the tampon and restrain its movement in the proximal direction. The undulations 130 of the ejector tube 126 slide over the tampon 140. Once the undulations 130 are withdrawn past the proximal or rear end of the tampon 140, portions 131 close towards each other so as to be positioned behind the tampon 140 for the start of the ejection operation (see FIG. 6).

The tubes 110 and 126 of the applicator are prevented from becoming disassembled during the activating or cocking step by a restraining means 124 and 134, or more preferably by means 234, 270 and 234.

After the ejector tube 126 has been pulled out to its operative position, the outer tube 110 is placed in the vaginal cavity. The ejector tube 126 is then telescoped back into the outer tube 110 towards the distal end thereof (see FIG. 6), pushing the tampon 140 through the central opening 118 and spreading open the yieldable petal sections 114. Because of the unidirectional nature of the flaps 122, tampon 140 is free to move in the distal direction.

The forward extent of travel of the ejector tube 126 through the outer tube 110 is limited by the optional circumferential flange 136 which abuts against the proximal edge of the outer tube 110. Since the ejector tube 126 is preferably slightly longer than the outer tube 110, the distal end of the ejector tube 126 extends beyond the distal end of the outer tube 110. This ensures that the tampon 140 will be completely discharged into the vaginal cavity. Alternatively, the tube 126 may even be slightly shorter than the outer tube 110, to thus make the overall length of the assembled applicator 108 (with stored tampon 140) even more compact. In this latter case, it has been typically found that the vaginal muscles adequately grasp the tampon to ensure proper withdrawal of the applicator with the tampon remaining properly lodged in place.

The flaps 122 can also be used in a conventional telescoping tampon applicator (where the ejector tube is stored behind the tampon 40, which latter is stored directly in the distal end of the outer tube). The flaps 122b then serve to hold the distal end of the tampon 40 in position to back up the petals 14 and prevent pinching caused by slots 16.

We claim:

1. A catamenial tampon applicator comprising:
    an ejector tube;
    an outer tube dimensioned to fit closely and telescopically over said ejector tube and having a distal discharge end;
    restraining means between said tubes for preventing the disassembly of said ejector tube from said outer tube in the proximal direction, comprising:
    a circumferentially-extending raised rib structure,
    a pair of circumferentially-extending raised rings, respectively being an outer stopping ring and an adjacent relatively-shorter inner stabilizing ring, the respective facing slopes of which at least partially define a valley therebetween,
    one of said rib structure or said pair being formed on the outer distal surface of said ejector tube and the other being formed on the inner proximal surface of said outer tube,
    said rib structure and said rings each being radially spaced from the tube other than the tube on which it is formed at least when said tubes are not in the telescopically collapsed position,
    said rib structure radially partially overlapping said pair by an amount such that the shorter stabilizing ring is aligned to make an interference fit with said rib structure and the taller stopping ring is aligned effectively to obstruct said rib structure from passing axially beyond said stopping ring in the proximal direction in normal use,
    said valley and said rib structure being compatibly shaped such that the latter is adapted to seat in said valley, to be captured between and to engage each of the facing slopes of said rings when seated therebetween, and to ride up the respective one of such slopes if axially displaced from the seated position in the direction of such one slope, whereby the restraining means stabilizes the tubes against relative wobble when said rib structure is seated in said valley.

2. An applicator according to claim 1, wherein said pair of rings is formed on said outer tube and said rib structure is formed on said ejector tube.

3. An applicator according to claim 2, wherein both of said tubes are made of molded plastic, and said ejector tube is adapted to store a tampon fitted therein with a small portion of said tampon extending from the distal end of said tube.

4. An applicator according to claim 3, wherein the distal end of the ejector tube is formed into a plurality of stubby fingers distally adjacent to said rib structure, and said fingers are each of a length less than the diameter of said ejector tube adjacent that structure, and said fingers being slightly curved inwardly sufficiently to engage positively and securely the proximal end of a tampon which might be snugly stored in the distal end of the ejector tube.

5. An applicator according to claim 4, wherein the stabilizing ring has a plateau of a width and the fingers are of a length sufficient to ensure that said fingers will engage said stabilizing ring plateau, if the respective axes of said tubes are at an angle greater than about 5°, to further stabilize the tubes.

6. An applicator according to claim 5, wherein the width of the bottom of said valley and matching rib structure are each about 0.02 inches, the height of the stabilizing ring above said valley is about 0.004 inches, the corresponding height of the stopping ring is about 0.01 inches, the slopes of the stabilizing ring are both about 30°, the distal slope of the stopping ring is about 35°, the distal slope of the rib structure matches that of the proximal slope of the stabilizing ring, the height of the rib structure is about 0.03 inches, and the width of the stabilizing ring is about 0.14 inches.

7. An applicator according to claim 3, wherein said rib structure is a plurality of ribs all of equal height and circumferentially separated one from the other by an spacing ranging from about 5° to about 15°.

8. An applicator according to claim 7, wherein said plastic has a stiffness of from 10,000 to 90,000 psi.

9. An applicator according to claim 7, wherein said valley in profile has a flat bottom, and said rib structure in profile has a matching flat plateau whose radius is substantially the same as that of said valley bottom.

10. An applicator according to claim 9, wherein the straight pull tube interlock strength is at least 1000 gms.

11. An applicator according to claim 10, wherein said plastic has a stiffness of from 10,000 to 40,000 psi.

12. An applicator according to claim 11, wherein the width of the flat bottom of the valley ranges from 0.010 to 0.025 inches.

13. An applicator according to claim 12, wherein the height of the stopping ring above the bottom of said valley is 3 to 5 times the height of the stabilizing ring above said bottom.

14. An applicator according to claim 13, wherein the distal slope of said stabilizing ring ranges from about 10° to about 35°, the proximal slope of stabilizing ring ranges from about 20° to about 35°, the distal slope of said stopping ring ranges from about 33° to about 60°, the proximal slope of said stopping ring ranges from about 15° to about 60°, the distal slope of the rib structure ranges from about being the same as the proximal slope of the stabilizing ring to about 90°, and the proximal slope of the rib structure ranges from about the same as the distal slope ring to about 90°.

15. A catamenial tampon and applicator assembly comprising an applicator according to claim 14,
further comprising a tampon stored in the distal end of said ejector tube, and
means fixed to the inside of the distal end of said outer tube and positioned at least closely adjacent a circumferentially continuous portion of said outer tube for gripping said extending portion of said tampon carried in said ejector tube so as to prevent proximal movement of such tampon relative to said outer tube during proximal withdrawal of the ejector tube over the tampon and yet also to permit distal ejection of such tampon from the outer tube, said means being at least one flap dimensioned relative to said outer tube to extend substantially more in the circumferential direction than in the axial direction and to extend inwardly sufficiently to engage said extending portion of said tampon carried in said ejector tube, said flap being flexible in the axial direction and being canted so as to have a circumferentially-aligned linear tip portion that is distally disposed relative to a respective base portion;
wherein there are at least three such inwardly directed flaps spaced and aligned at substantially equal intervals around the circumference of the inner surface of said outer tube, and said flaps are of a substantially flat blade-shape and are canted distally at an angle to the axis of said outer tube which ranges from 10° to 80°;
wherein the distal end of the ejector tube is formed into a plurality of stubby fingers distally adjacent to said rib structure, and said fingers are each of a length less than the diameter of said ejector tube adjacent that structure, with spacing between said fingers being less than the circumferential extent of any one of said flaps, and said fingers being slightly curved inwardly sufficiently to engage positively and securely the proximal end of said tampon stored in the distal end of the ejector tube;
wherein said distal end of said outer tube includes a plurality of petal sections which are shaped to form a substantially rounded tip and are sufficiently flexible to pass a tampon therethrough; and
wherein said tampon has a slightly enlarged head in the extending portion of the tampon with abrupt shoulders located distally adjacent said flaps.

16. An applicator according to claim 3, wherein said valley in profile has a flat bottom, and said rib structure in profile has a matching flat plateau whose radius is substantially the same as that of said valley bottom.

17. An applicator according to claim 16, wherein the width of the flat bottom of the valley ranges from 0.010 to 0.025 inches.

18. An applicator according to claim 16, wherein the height of the stopping ring above the bottom of said valley is 3 to 5 times the height of the stabilizing ring above said bottom.

19. A catamenial tampon applicator comprising:
a molded plastic ejector tube adapted to store a tampon fitted therein with a small portion of said tampon extending from the distal end of said tube;
a molded plastic outer tube dimensioned to fit closely and telescopically over said ejector tube and having a distal discharge end;
means fixed to the inside of the distal end of said outer tube and positioned at least closely adjacent a circumferentially continuous portion of said outer tube for gripping said extending portion of a tampon carried in said ejector tube so as to prevent proximal movement of such tampon relative to said outer tube during proximal withdrawal of the ejector tube over the tampon and yet also to permit distal ejection of such tampon from the outer tube, said means being at least one flap dimensioned relative to said outer tube to extend substantially more in the circumferential direction than in the axial direction and to extend inwardly sufficiently to engage said extending portion of a tampon carried in said ejector tube, said flap being flexible in the axial direction and being canted so as to have a circumferentially-aligned linear tip portion that is distally disposed relative to a respective base portion,
restraining means between said tubes for preventing the disassembly of said ejector tube from said outer tube in the proximal direction, comprising
a circumferentially-extending raised rib structure,
a pair of circumferentially-extending raised rings, respectively being an outer stopping ring and an adjacent relatively-shorter inner stabilizing ring, the respective facing slopes of which at least partially define a valley therebetween,
one of said rib structure or said pair being formed on the outer distal surface of said ejector tube and the other being formed on the inner proximal surface of said outer tube,
said rib structure and said rings each being radially spaced from the tube other than the tube on which it is formed,
said rib structure radially partially overlapping said pair by an amount such that the shorter stabilizing ring is aligned to make an interference fit with said rib structure and the taller stopping ring is aligned effectively to obstruct said rib structure from passing axially beyond said stopping ring in the proximal direction in normal use,
said valley and said rib structure being compatibly shaped such that the latter is adapted to seat in said valley, to be captured between and to engage each of the facing slopes of said rings when seated therebetween, and to ride up the respective one of such slopes if axially displaced from the seated position in the direction of such one slope, whereby the restraining means stabilizes the tubes against relative wobble when said rib structure is seated in said valley.

20. An applicator according to claim 19, wherein there are at least three such inwardly directed flaps spaced and aligned at substantially equal intervals around the circumference of the inner surface of said outer tube, and said flaps are of a substantially flat blade-shape and are canted distally at an angle to the axis of said outer tube which ranges from 10° to 80°.

21. An applicator according to claim 20, wherein said distal end of said outer tube includes a plurality of petal sections which are shaped to form a substantially rounded tip and are sufficiently flexible to pass a tampon therethrough.

22. A catamenial tampon and applicator assembly comprising an applicator according to claim 21, further comprising a tampon stored in the distal end of said ejector tube and wherein said tampon has a slightly enlarged head in the extending portion of the tampon with abrupt shoulders located distally adjacent said flaps.

* * * * *